(12) United States Patent
Sawada et al.

(10) Patent No.: US 7,828,877 B2
(45) Date of Patent: Nov. 9, 2010

(54) SEPARATION OF CARBON DIOXIDE FROM OTHER GASES

(75) Inventors: James A. Sawada, Vancouver (CA); Matthew L. Babicki, West Vancouver (CA); Amy Chiu, Richmond (CA); Andre Boulet, Vancouver (CA); Surajit Roy, Burnaby (CA); Edward J. Rode, Surrey (CA)

(73) Assignee: Xebec Adsorption, Inc., Burnaby, B.C. (CA)

( * ) Notice: Subject to any disclaimer, the term of this patent is extended or adjusted under 35 U.S.C. 154(b) by 630 days.

(21) Appl. No.: 11/667,041

(22) PCT Filed: Nov. 7, 2005

(86) PCT No.: PCT/US2005/040375
§ 371 (c)(1),
(2), (4) Date: May 3, 2007

(87) PCT Pub. No.: WO2006/052937
PCT Pub. Date: May 18, 2006

(65) Prior Publication Data
US 2007/0261551 A1 Nov. 15, 2007

Related U.S. Application Data

(60) Provisional application No. 60/625,202, filed on Nov. 5, 2004.

(51) Int. Cl.
*B01D 53/02* (2006.01)
(52) U.S. Cl. ............... 95/96; 95/139; 96/130; 96/132

(58) Field of Classification Search ................ 95/96, 95/100, 139, 121, 130, 131, 132
See application file for complete search history.

(56) References Cited

U.S. PATENT DOCUMENTS 3,094,569 A 6/1963 Thomas (Continued)

FOREIGN PATENT DOCUMENTS

CA 1256038 6/1989

(Continued)

OTHER PUBLICATIONS

Carvill et al., "Sorption Enhanced Reaction Process," *AIChE Journal* 42(10):2765-2772, 1996.

(Continued)

*Primary Examiner*—Robert A Hopkins
(74) *Attorney, Agent, or Firm*—Klarquist Sparkman, LLP

(57) ABSTRACT

An inventive adsorptive gas separation process is provided capable of producing a purified methane product gas as a light non-adsorbed product gas as opposed to a heavy desorbed exhaust gas component, from a feed gas mixture comprising at least methane, and carbon dioxide. In an embodiment of the invention, the feed gas mixture may comprise at least about 10% carbon dioxide, and the purified methane product gas may be desirably purified to contain less than about 5000 ppm carbon dioxide. In another embodiment of the invention, the feed gas mixture may comprise at least about 50% carbon dioxide, and the purified methane product gas may be desirably purified to contain less than about 5000 ppm carbon dioxide.

21 Claims, 1 Drawing Sheet

U.S. PATENT DOCUMENTS

| | | | |
|---|---|---|---|
| 3,204,388 A | 9/1965 | Asker |
| 3,430,418 A | 3/1969 | Wagner |
| 3,513,631 A | 5/1970 | Siebert et al. |
| 3,564,816 A | 2/1971 | Batta |
| 3,594,984 A | 7/1971 | Toyama et al. |
| 3,751,878 A | 8/1973 | Collins |
| 3,847,672 A | 11/1974 | Trocciola et al. |
| 3,865,924 A | 2/1975 | Gidaspow et al. |
| 4,019,879 A | 4/1977 | Rabo et al. |
| 4,077,779 A | 3/1978 | Sircar et al. |
| 4,144,037 A | 3/1979 | Armond et al. |
| 4,153,434 A | 5/1979 | Settlemyer |
| 4,200,682 A | 4/1980 | Sederquist |
| 4,272,265 A | 6/1981 | Snyder |
| 4,322,394 A | 3/1982 | Mezey et al. |
| 4,354,859 A | 10/1982 | Keller, II et al. |
| 4,406,675 A | 9/1983 | Dangieri et al. |
| 4,452,612 A | 6/1984 | Mattia |
| 4,530,705 A | 7/1985 | Firey |
| 4,532,192 A | 7/1985 | Baker et al. |
| 4,553,981 A | 11/1985 | Fuderer |
| 4,555,453 A | 11/1985 | Appleby |
| 4,578,214 A | 3/1986 | Jungerhans |
| 4,587,114 A | 5/1986 | Hirai et al. |
| 4,595,642 A | 6/1986 | Nakanishi et al. |
| 4,696,682 A | 9/1987 | Hirai et al. |
| 4,702,903 A | 10/1987 | Keefer |
| 4,726,816 A | 2/1988 | Fuderer |
| 4,743,276 A | 5/1988 | Nishida et al. |
| 4,758,253 A | 7/1988 | Davidson et al. |
| 4,759,997 A | 7/1988 | Ohyauchi et al. |
| 4,781,735 A | 11/1988 | Tagawa et al. |
| 4,783,433 A | 11/1988 | Tajima et al. |
| 4,790,858 A | 12/1988 | Sircar |
| 4,801,308 A | 1/1989 | Keefer |
| 4,816,121 A | 3/1989 | Keefer |
| 4,857,083 A | 8/1989 | DiMartino |
| 4,914,076 A | 4/1990 | Tsuji et al. |
| 4,915,771 A | 4/1990 | O'Brien et al. |
| 4,917,711 A | 4/1990 | Xie et al. |
| 4,963,339 A | 10/1990 | Krishnamurthy et al. |
| 4,968,329 A | 11/1990 | Keefer |
| 4,969,935 A | 11/1990 | Hay |
| 4,988,580 A | 1/1991 | Ohsaki et al. |
| 4,994,331 A | 2/1991 | Cohen |
| 5,068,159 A | 11/1991 | Konoshita |
| 5,079,103 A | 1/1992 | Schramm |
| 5,082,473 A | 1/1992 | Keefer |
| 5,096,469 A | 3/1992 | Keefer |
| 5,096,470 A | 3/1992 | Krishnamurthy |
| 5,126,310 A | 6/1992 | Golden et al. |
| 5,133,784 A | 7/1992 | Boudet et al. |
| 5,147,735 A | 9/1992 | Ippommatsu et al. |
| 5,175,061 A | 12/1992 | Hildebrandt et al. |
| 5,227,598 A | 7/1993 | Woodmansee et al. |
| 5,245,110 A | 9/1993 | Van Dijk et al. |
| 5,246,676 A | 9/1993 | Hay |
| 5,248,325 A | 9/1993 | Kagimoto et al. |
| 5,256,172 A | 10/1993 | Keefer |
| 5,256,174 A | 10/1993 | Kai et al. |
| 5,258,571 A | 11/1993 | Golden et al. |
| 5,271,916 A | 12/1993 | Vanderborgh et al. |
| 5,282,886 A | 2/1994 | Kobayashi et al. |
| 5,328,503 A | 7/1994 | Kumar et al. |
| 5,360,679 A | 11/1994 | Buswell et al. |
| 5,366,818 A | 11/1994 | Wilkinson et al. |
| 5,393,326 A | 2/1995 | Engler et al. |
| 5,411,578 A | 5/1995 | Watson et al. |
| 5,411,721 A * | 5/1995 | Doshi et al. ............... 423/220 |
| 5,415,748 A | 5/1995 | Emiliani et al. |
| 5,429,665 A | 7/1995 | Botich |
| 5,431,716 A | 7/1995 | Ebbeson |
| 5,434,016 A | 7/1995 | Benz et al. |
| 5,441,559 A | 8/1995 | Petit et al. |
| 5,487,775 A | 1/1996 | LaCava et al. |
| 5,509,956 A | 4/1996 | Opperman et al. |
| 5,523,326 A | 6/1996 | Dandekar et al. |
| 5,529,763 A | 6/1996 | Peng et al. |
| 5,529,970 A | 6/1996 | Peng |
| 5,531,809 A | 7/1996 | Golden et al. |
| 5,543,238 A | 8/1996 | Strasser |
| 5,579,610 A | 12/1996 | Jackson |
| 5,593,478 A | 1/1997 | Hill et al. |
| 5,604,047 A | 2/1997 | Bellows et al. |
| 5,632,807 A | 5/1997 | Tomita et al. |
| 5,645,950 A | 7/1997 | Benz et al. |
| 5,646,305 A | 7/1997 | Wagner et al. |
| 5,656,067 A | 8/1997 | Watson et al. |
| 5,658,370 A | 8/1997 | Vigor et al. |
| 5,711,926 A | 1/1998 | Knaebel |
| 5,714,276 A | 2/1998 | Okamoto |
| 5,766,311 A | 6/1998 | Ackley et al. |
| 5,810,909 A | 9/1998 | Notaro et al. |
| 5,811,201 A | 9/1998 | Skowronski |
| 5,827,358 A | 10/1998 | Kulish et al. |
| 5,840,099 A | 11/1998 | Kratz et al. |
| 5,876,486 A | 3/1999 | Steinwandel et al. |
| 5,891,217 A | 4/1999 | Lemcoff et al. |
| 5,900,329 A | 5/1999 | Reiter et al. |
| 5,917,136 A | 6/1999 | Gaffney et al. |
| 5,925,322 A | 7/1999 | Werth |
| 5,938,819 A | 8/1999 | Seery |
| 5,955,039 A | 9/1999 | Dowdy |
| 5,958,109 A | 9/1999 | Fuderer |
| 5,968,680 A | 10/1999 | Wolfe et al. |
| 5,980,857 A | 11/1999 | Kapoor et al. |
| 5,981,096 A | 11/1999 | Hornburg et al. |
| 5,998,056 A | 12/1999 | Divisek et al. |
| 6,022,399 A | 2/2000 | Ertl et al. |
| 6,045,933 A | 4/2000 | Okamoto |
| 6,051,050 A | 4/2000 | Keefer et al. |
| 6,056,804 A | 5/2000 | Keefer et al. |
| 6,060,032 A | 5/2000 | Hable et al. |
| 6,063,161 A | 5/2000 | Keefer et al. |
| 6,077,620 A | 6/2000 | Pettit |
| 6,090,312 A | 7/2000 | Ziaka et al. |
| 6,143,057 A | 11/2000 | Bülow et al. |
| 6,162,558 A | 12/2000 | Borup et al. |
| 6,176,897 B1 | 1/2001 | Keefer |
| 6,190,623 B1 | 2/2001 | Sanger et al. |
| 6,190,791 B1 | 2/2001 | Hornburg |
| 6,200,365 B1 | 3/2001 | Eimer et al. |
| 6,210,822 B1 | 4/2001 | Abersfelder et al. |
| 6,231,644 B1 | 5/2001 | Jain et al. |
| 6,255,010 B1 | 7/2001 | George et al. |
| 6,283,723 B1 | 9/2001 | Milburn et al. |
| 6,293,998 B1 | 9/2001 | Dolan et al. |
| 6,296,823 B1 | 10/2001 | Ertl et al. |
| 6,312,843 B1 | 11/2001 | Kimbara et al. |
| 6,358,300 B1 | 3/2002 | Fornof et al. |
| 6,358,302 B1 | 3/2002 | Deng et al. |
| 6,398,853 B1 | 6/2002 | Keefer et al. |
| 6,406,523 B1 | 6/2002 | Connor et al. |
| 6,428,915 B1 | 8/2002 | Ban et al. |
| 6,471,748 B1 | 10/2002 | Ackley |
| 6,607,854 B1 | 8/2003 | Rehg et al. |
| 6,610,124 B1 | 8/2003 | Dolan et al. |
| 6,667,128 B2 | 12/2003 | Edlund |
| 6,692,545 B2 | 2/2004 | Gittleman et al. |
| 6,902,602 B2 | 6/2005 | Keefer et al. |
| 6,921,597 B2 | 7/2005 | Keefer et al. |
| 7,041,272 B2 | 5/2006 | Keefer et al. |
| 7,087,331 B2 | 8/2006 | Keefer et al. |
| 7,097,925 B2 | 8/2006 | Keefer |

| | | | |
|---|---|---|---|
| 2001/0047824 A1 | 12/2001 | Hill et al. | |
| 2002/0004157 A1 | 1/2002 | Keefer et al. | |
| 2002/0098394 A1 | 7/2002 | Keefer et al. | |
| 2002/0104518 A1 | 8/2002 | Keefer et al. | |
| 2002/0110503 A1 | 8/2002 | Gittleman et al. | |
| 2002/0110504 A1 | 8/2002 | Gittleman et al. | |
| 2002/0112479 A1 | 8/2002 | Keefer et al. | |
| 2002/0127442 A1 | 9/2002 | Connor et al. | |
| 2002/0142198 A1 | 10/2002 | Towler et al. | |
| 2002/0142208 A1 | 10/2002 | Keefer et al. | |
| 2003/0143448 A1 | 7/2003 | Keefer et al. | |
| 2003/0157390 A1 | 8/2003 | Keefer et al. | |
| 2004/0005492 A1 | 1/2004 | Keefer et al. | |
| 2004/0131912 A1 | 7/2004 | Keefer et al. | |
| 2004/0197612 A1 | 10/2004 | Keefer et al. | |
| 2005/0284291 A1 | 12/2005 | Alizadeh-Khiavi | |
| 2007/0068386 A1 | 3/2007 | Mitariten | |

FOREIGN PATENT DOCUMENTS

| | | | |
|---|---|---|---|
| CA | 2016045 | | 8/1994 |
| CA | 2109055 | | 4/1995 |
| CA | 2087972 | | 1/2000 |
| CA | 2087973 | | 1/2001 |
| CA | 2325072 | | 4/2002 |
| DE | 3913581 | A1 | 10/1990 |
| EP | 0 143 537 | A2 | 6/1985 |
| EP | 0 341 189 | A1 | 11/1989 |
| EP | 0 345 908 | | 12/1989 |
| EP | 0 143 537 | B1 | 3/1990 |
| EP | 0 681 860 | A2 | 11/1995 |
| EP | 0 691 701 | A1 | 1/1996 |
| EP | 0 737 648 | | 10/1996 |
| EP | 0 750 361 | A | 12/1996 |
| EP | 0 751 045 | | 1/1997 |
| EP | 0 853 967 | | 7/1998 |
| EP | 1 070 531 | A2 | 1/2001 |
| EP | 1 095 689 | A1 | 5/2001 |
| EP | 1 172 772 | | 1/2002 |
| GB | 2 042 365 | | 9/1980 |
| JP | 59075574 | A | 4/1984 |
| JP | 62274561 | | 11/1987 |
| JP | 62278770 | | 12/1987 |
| JP | 63034862 | | 2/1988 |
| JP | 63166137 | | 7/1988 |
| JP | 63228572 | A | 9/1988 |
| JP | 04206161 | A | 7/1992 |
| JP | 05166528 | | 7/1993 |
| JP | 07094200 | | 7/1995 |
| JP | 8045526 | A2 | 2/1996 |
| JP | 10027621 | A | 1/1998 |
| JP | 10325360 | A | 12/1998 |
| JP | 11214021 | A2 | 8/1999 |
| JP | 2002 358972 | | 12/2002 |
| WO | WO 94/04249 | | 3/1994 |
| WO | WO 96/13871 | | 5/1996 |
| WO | WO 98/29182 | | 7/1998 |
| WO | WO 99/01202 | | 1/1999 |
| WO | WO 99/16249 | | 4/1999 |
| WO | WO 99/28013 | | 6/1999 |
| WO | WO 99/46032 | | 9/1999 |
| WO | WO 00/16425 | | 3/2000 |
| WO | WO 00/16880 | | 3/2000 |
| WO | WO 00/76628 | | 12/2000 |
| WO | WO 00/76630 | | 12/2000 |
| WO | WO 01/47050 | | 6/2001 |
| WO | WO 02/24309 | | 3/2002 |
| WO | WO 02/35623 | | 5/2002 |
| WO | WO 02/37590 | | 5/2002 |
| WO | WO 02/45821 | | 6/2002 |
| WO | WO 02/47797 | | 6/2002 |
| WO | WO 02/056400 | | 7/2002 |
| WO | WO 03/020674 | | 3/2003 |
| WO | WO 03/077339 | | 9/2003 |
| WO | WO 2004/030130 | | 4/2004 |

OTHER PUBLICATIONS

Ding et al., "Equilibria and Kinetics of CO2 Adsorption on Hydrotalcite Adsorbent," *Chemical Engineering Science* 55:3461-3474, 2000.

Ding et al., "Adsorption-Enhanced Steam-Methane Reforming," *Chemical Engineering Science* 55:3929-3940, 2000.

Iyuke et al., "Application of Sn-Activated Carbon in Pressure Swing Adsorption for Purification of H2," *Chemical Engineering Science* 55:4745-4755, 2000.

Vaporciyan and Kadlec, "Periodic Separating Reactors: Experiments and Theory," *AIChE Journal* 35:831-844, 1989.

International Search Report from International Application No. PCT/CA99/00823, Feb. 11, 2000.

Wills et al., "Production of Pipeline-Quality Natural Gas with the Molecular Gate $CO_2$ Removal Process," *SPE Production & Facilities*, pp. 4-8, Feb. 2004.

Carson, "Thermodynamics of Pressure Swing Adsorption (PSA) in the Recovery of Residual Hydrogen from SOFC Anode Gas," *Proceedings of the 30$^{th}$ Intersociety Energy Conversion Engineering Conference*, ASME, New York, New York, 3:229-234, 1995.

Chatsiriwech et al., "Enhancement of Catalytic Reaction by Pressure Swing Adsorption," *Catalysis Today* 20:351-366, 1994.

"Fuel Cells for Transportation 98," National Laboratory Annual Progress Report (1998), U.S. Department of Energy, Office of Advanced Automotive Technologies, "CO Clean-up R&D," Argonne National Laboratory, pp. 33-36.

Hufton et al., "Sorption Enhanced Reaction Process for Hydrogen Production," *AIChE Journal* 45(2):248-256, 1999.

International Search Report from International Application No. PCT/CA02/00368, Aug. 12, 2002.

International Search Report from International Application No. PCT/CA2003/000371, Sep. 21, 2004.

International Search Report from International Application No. PCT/CA2004/000289, Dec. 27, 2005.

* cited by examiner

SEPARATION OF CARBON DIOXIDE FROM OTHER GASES

CROSS REFERENCE TO RELATED APPLICATIONS

This is the U.S. National Stage of International Application No. PCT/US2005/040375, filed Nov. 5, 2004, which was published in English under PCT Article 21(2), which in turn claims the benefit of U.S. Provisional Application No. 60/625,202, filed Nov. 5, 2004, which are incorporated herein in their entirety.

FIELD

The present disclosure relates to processes for the separation of carbon dioxide from other gases, and more particularly to processes for the separation of carbon dioxide from methane-containing gas mixtures.

BACKGROUND

Adsorptive separation systems are known for use in separation of gas streams comprising multiple gas components. Pressure swing, temperature swing, and partial pressure swing or displacement purge adsorption are exemplary processes known in the art for performing such separations of multi-component gas mixtures. In the exemplary case of separation of methane-containing gas mixtures, existing adsorption based separation processes do not provide for desirably efficient separation of methane from other gas components. Existing adsorptive methane separation processes typically include sequential pressure or temperature swing adsorption systems requiring multiple adsorption steps and corresponding multiple adsorption systems or subsystems, and typically result in the delivery of product methane gas streams at relatively low pressure, commonly as a component of desorption exhaust. Existing processes may also result in delivery of methane product gas at relatively low purity and/or recovery due to the lack of efficiency in adsorptively separating methane from other common gas mixture components. Such other common gas mixture components may for example comprise carbon dioxide, nitrogen and oxygen in impure methane-containing feed gas streams. Examples of such impure methane-containing gas streams may include biogas, landfill gas, impure natural gas or other methane-containing commercial gas streams. In applications where such impure methane streams are desired to be stored and used as compressed or liquified gas fuels, the relatively low purity of the methane product streams typically produced by some existing adsorptive separation processes may result in inefficiencies and/or impracticalities in the compression and/or liquifaction processes used to store such fuel gases.

SUMMARY

Disclosed herein are inventive adsorptive gas separation processes that addresses some shortcomings of the prior art. In one embodiment, an adsorptive gas separation process is provided capable of producing a purified methane product gas as a light non-adsorbed product gas (as opposed to a heavy desorbed exhaust gas component) from a feed gas mixture comprising at least methane, and carbon dioxide. In an exemplary embodiment, the feed gas mixture may comprise at least about 10% carbon dioxide, and the purified methane product gas may be desirably purified to contain less than about 5000 ppm carbon dioxide. In another exemplary embodiment, the feed gas mixture may comprise at least about 20% carbon dioxide, and the purified methane product gas may be desirably purified to contain less than about 5000 ppm carbon dioxide. In yet a further exemplary embodiment, the feed gas mixture may comprise at least about 50% carbon dioxide, and the purified methane product gas may be desirably purified to contain less than about 5000 ppm carbon dioxide. In any of the preceding exemplary embodiments, the purified methane product gas may be more desirably purified to contain less than about 1000 ppm carbon dioxide, and most desirably less than 100 ppm carbon dioxide.

In another embodiment, an adsorptive gas separation process is provided capable of producing a purified methane product gas at a recovery of at least about 50% in a single adsorption step with a single adsorption device, from a feed gas mixture comprising at least methane and carbon dioxide. In an exemplary embodiment, the feed gas mixture may comprise at least about 10% carbon dioxide, and the purified methane product gas may be desirably purified to contain less than about 5000 ppm carbon dioxide. In another exemplary embodiment, the feed gas mixture may comprise at least about 20% carbon dioxide, and in yet another exemplary embodiment, may comprise at least about 50% carbon dioxide. In any of the preceding exemplary embodiments, the purified methane product gas may be more desirably purified to contain less than about 1000 ppm carbon dioxide, and most desirably less than 100 ppm carbon dioxide.

In a further embodiment, an adsorptive gas separation process is provided capable of producing purified methane product gas from a feed gas mixture comprising at least methane and carbon dioxide, by adsorption of the feed gas mixture in an adsorber in contact with at least a first adsorbent material suited for adsorbing at least a majority of the carbon dioxide in the feed gas stream, and a second adsorbent material suited for substantially removing remaining amounts of carbon dioxide while substantially excluding methane from adsorption. In an exemplary embodiment, the feed gas mixture may comprise at least about 10% carbon dioxide, and the purified methane product gas may be desirably purified to contain less than about 5000 ppm carbon dioxide. In a further exemplary embodiment, the feed gas mixture may comprise at least about 20% carbon dioxide, and in yet another exemplary embodiment, may comprise at least about 50% carbon dioxide. In any of the preceding exemplary embodiments, the purified methane product gas may be more desirably purified to contain less than about 1000 ppm carbon dioxide, and most desirably less than 100 ppm carbon dioxide.

In a further embodiment, an adsorptive gas separation process is provided capable of providing enriched methane product gas from a feed gas mixture comprising at least methane and carbon dioxide, by adsorption of at least a majority of the carbon dioxide on an alumina-based adsorbent material to produce the enriched methane product gas. In an exemplary embodiment, the feed gas stream may comprise at least about 15% carbon dioxide, and the enriched methane product gas stream may desirably comprise less than about 5% carbon dioxide. In a further exemplary embodiment, the feed gas stream may comprise at least about 25% carbon dioxide, and the enriched methane product gas stream may desirably comprise less than about 5% carbon dioxide. In yet a further exemplary embodiment, the feed gas stream may comprise at least about 50% carbon dioxide.

DETAILED DESCRIPTION OF SEVERAL EMBODIMENTS

Figure 1:
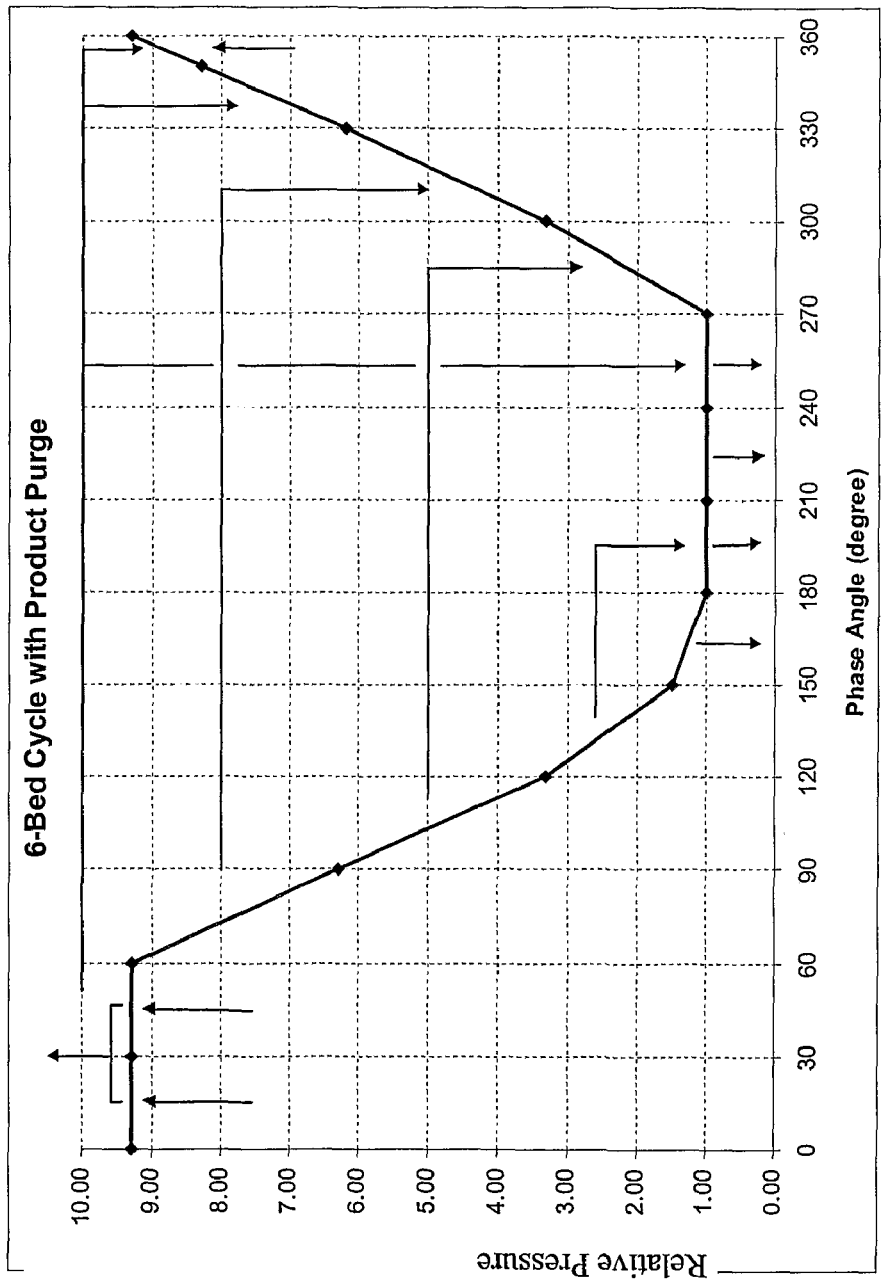
FIG. 1 shows a purely exemplary 6 bed pressure swing adsorption (PSA) cycle comprising a single common adsorber pressure profile (i.e., relative pressure vs. phase angle) suitable for implementing an embodiment of the presently disclosed adsorption processes using PSA techniques. As is known in the art, the "phase angle" of a PSA cycle is employed to divide the progress of a one complete cycle into 360° to be able to determine the implementation of each individual step during the cycle.

In an above-mentioned embodiment, the inventive process may be used to produce a relatively purified methane product gas stream by adsorption from an impure methane containing feed gas additionally comprising at least about 10% carbon dioxide, where the purified methane product is produced as the light, non-adsorbed product gas, and delivered at the pressure of the adsorption process. In another exemplary embodiment, the feed gas may comprise at least about 20% carbon dioxide. The purified methane product gas may desirably be purified to comprise less than about 5000 ppm of carbon dioxide, more desirably to comprise less than about 1000 ppm carbon dioxide, and in particular may be purified to comprise less than about 100 ppm carbon dioxide, such as is desirable for use in some commercial applications such as the liquifaction of methane gas for storage as a liquified gas fuel. In an exemplary embodiment, the inventive adsorption process may comprise a pressure swing adsorption (PSA) process wherein the feed gas mixture may be passed over an adsorbent material to produce a non-adsorbed product gas delivered at a higher pressure, and a desorbed exhaust gas delivered at a lower pressure of the process, wherein the purified methane product gas (comprising desirably less than about 5000 ppm carbon dioxide, or more desirably less than about 1000 ppm carbon dioxide, or particularly less than about 100 ppm carbon dioxide) may be delivered as the non-adsorbed product gas.

Common impure methane feed gas mixtures may additionally comprise gas components other than methane and carbon dioxide, which may include for example, and without limitation, nitrogen and oxygen. In addition to the removal of carbon dioxide from the purified methane product gas, the present inventive process may also be used to desirably purify the methane product gas by substantially reducing the concentration of oxygen in the methane product gas relative to the feed gas mixture, such as is desirable to reduce oxygen concentration in the purified methane product gas in applications where oxygen levels may become a safety concern in downstream uses of the methane product gas. This may be the case in liquifaction applications where oxygen in the methane product may become concentrated during the liquifaction process to produce a liquified methane fuel.

In a further embodiment, as summarized above, the inventive process may be used to produce a purified methane product gas from a feed gas mixture comprising at least methane and carbon dioxide by adsorption of at least a portion of the carbon dioxide component in a single pass through the adsorption process, in a single adsorption device, wherein the methane product gas is purified to contain less than about 5000 ppm carbon dioxide while recovering at least about 50% of the methane in the feed gas. In one example, a purified methane product gas may be obtained with a gas flow path through a single adsorption process unit represented by a single adsorber element (which may or may not include a single adsorbent bed provided the multiple beds are contiguous with each other along the gas flow path). In other words, a purified methane product gas may be obtained without having to introduce a feed gas into a first adsorbent element to obtain an intermediate product that is subsequently introduced into a second adsorber element In an exemplary such embodiment, the feed gas mixture may comprise at least about 10% carbon dioxide, and the purified methane product gas may desirably be further purified to contain less than about 1000 ppm carbon dioxide, and particularly less than about 100 ppm carbon dioxide, such as is desirable for liquifaction of the purified methane product gas for storage as a liquified methane fuel gas. In a further exemplary embodiment, the feed gas mixture may comprise at least about 20% carbon dioxide, and in a yet further exemplary embodiment, the feed gas mixture may comprise at least about 50% carbon dioxide. Additionally, the present inventive adsorptive separation process may be used to desirably produce a purified methane product gas containing less than about 5000 ppm carbon dioxide at a recovery of at least about 65% and particularly at a recovery of at least 75% of the methane in the feed gas mixture.

In a further embodiment of the present inventive adsorptive gas separation processes, multiple adsorbent materials in a single adsorber unit or element may be used to produce the desired purified methane product gas from the feed gas mixture comprising at least methane and carbon dioxide by means of adsorptive separation. In an exemplary embodiment, a first adsorbent material may be used to adsorb at least a majority of the carbon dioxide from the feed gas mixture. Such first adsorbent material may be selected from suitable adsorbent materials either known in the art, or developed in the future, such suitable adsorbent materials having both desirably high adsorptive capacities for adsorption of carbon dioxide, and relatively low adsorptive capacity for methane, resulting in a distinct selectivity for adsorption of carbon dioxide in preference to methane. Such suitable adsorbent materials may comprise for example, and without limitation, aluminas, silicas, hydrophobic zeolites (such as zeolite Y or ZSM-5 for example), activated carbon, and combinations thereof. In particular, activated alumina and silica gel, or a combination thereof may desirably be applied to the inventive process as a suitable first adsorbent material, as they both demonstrate desirably high adsorptive carbon dioxide capacity and relatively low adsorptive methane capacity, and are therefore selective for the adsorption of carbon dioxide over methane. In a further exemplary embodiment, silica gel followed in the adsorption path by activated alumina may be used as a first adsorbent material in the inventive processes. A second adsorbent material may be used in the present inventive adsorptive gas separation processes to adsorb any remaining portion of carbon dioxide in the process gas stream following adsorption of at least a majority of the carbon dioxide from the feed gas mixture by the first adsorbent material. In order to substantially adsorb the remaining portion of carbon dioxide, the second adsorbent material may be selected from any suitable adsorbent materials known in the art, or subsequently developed, such suitable adsorbent materials having a desirably high adsorptive selectivity for carbon dioxide relative to methane. In particular, adsorbent materials with very high adsorptive selectivities for carbon dioxide over methane to the point of substantially excluding methane from adsorption on the adsorbent material may be preferably selected for use as the second adsorbent material in the inventive processes. Such suitable second adsorbent materials may comprise for example, and without limitation, zeolite 3A, carbon molecular sieves, titanosilicate molecular sieve materials (also known as mixed tetrahedral/octahedral molecular sieve materials) and combinations thereof. More desirably, such suitable second adsorbent materials may comprise carbon molecular sieves, titanosilicate molecular sieves materials (such as ETS-4 for example), and combinations thereof, wherein such more desirable second adsorbent materials may be prepared to substantially exclude methane from adsorption while actively adsorbing carbon dioxide. In all cases, suitable adsorbent materials for application in any of the embodiments may be formed into any suitable shape or form for adsorption of gas components in a suitable adsorption apparatus, such forms which may comprise for example, and without limitation, powders, pellets, beads, sheets and particularly thin sheets, cloths, fabrics or combinations thereof, such as are known in the art or hereafter developed for use in adsorption processes.

In embodiments of the present inventive gas separation processes adapted to pressure swing adsorption (PSA) techniques, a maximum, or higher pressure for the PSA process may be selected that desirably provides for both bulk adsorption of at least a majority of the carbon monoxide on the first adsorbent material in the PSA adsorbers, and adsorption of substantially any remaining amounts of carbon dioxide on the second adsorbent material in the PSA adsorbers. In an exemplary embodiment of the inventive processes adapted for PSA, such suitable maximum PSA pressure may be desirably chosen to be between about 100-250 psig and more desirably between about 130-230 psig. In further embodiments adapted for PSA, a minimum, or lower PSA pressure may be chosen that desirably provides for the desorption of adsorbed gas components from the adsorbent material(s) during regeneration of the PSA adsorbers between adsorption cycles. Such minimum PSA pressure may be chosen as ambient pressure, or in an exemplary embodiment comprising vacuum assisted desorption of the PSA adsorbers, such minimum pressure may be desirably chosen to be below ambient pressure.

An exemplary, and non-limiting PSA adsorber pressure profile suitable for adaptation of the present inventive adsorptive separation processes to a 6-adsorber PSA device for the purification of a methane product gas by PSA from a feed gas mixture comprising at least methane and carbon dioxide components is illustrated in FIG. 1. The relative pressure levels of various stages of the exemplary PSA cycle for a single PSA adsorber vessel are shown against the progressive phase of the cycle, wherein the progressive phase of the 6-adsorber PSA cycle are represented as 12 half-steps. The disclosed pressure cycle comprises three depressurization steps, and three re-pressurization steps, and both a supply purge stream and a product purge stream in order to desirably increase the recovery of methane in the purified methane product gas, relative to some simpler PSA cycles, such as are known in the art, which may employ product purge alone to regenerate the adsorbent materials.

In view of the many possible embodiments to which the principles of this disclosure may be applied, it should be recognized that the illustrated embodiments are only preferred examples and should not be taken as limiting the scope of the invention.

What is claimed is:

1. An adsorptive gas separation process for producing a purified methane product gas from a feed gas mixture comprising at least methane and carbon dioxide, wherein the feed gas mixture comprises at least about 10% carbon dioxide, and the purified methane product gas is produced by adsorption of the feed gas mixture in an adsorber in contact with at least a first adsorbent material suited for adsorbing at least a majority of the carbon dioxide in the feed gas stream, and subsequently a second adsorbent material suited for substantially removing remaining amounts of carbon dioxide while substantially excluding methane from adsorption, and wherein the purified methane product gas contains less than about 5000 ppm carbon dioxide, wherein the first adsorbent material is selected from the group consisting of aluminas, silicas, silica gel, hydrophohic zeolites, activated carbon and combinations thereof and the second adsorbent material is selected from the group consisting of zeolite 3A, carbon molecular sieves, titanosilicate molecular sieve materials and combinations thereof, and the separation process further includes vacuum assisted desorption of the adsorber during regeneration of the adsorber.

2. The adsorptive gas separation process according to claim 1 wherein the feed gas mixture comprises at least about 20% carbon dioxide.

3. The adsorptive gas separation process according to claim 1 wherein the feed gas mixture comprises at least about 50% carbon dioxide.

4. The adsorptive gas separation process according to claim 1 wherein the purified methane product gas contains less than about 1000 ppm of carbon dioxide.

5. The adsorptive gas separation process according to claim 1 wherein the purified methane product gas contains less than about 100 ppm of carbon dioxide.

6. The adsorptive gas separation process according to claim 1 wherein the adsorptive gas separation process comprises a pressure swing adsorption process.

7. The adsorptive gas separation process according to claim 6 wherein the pressure swing adsorption process defines a higher pressure and a lower pressure, and wherein the higher pressure is between about 100-250 psig.

8. The adsorptive gas separation process according to claim 6 wherein the pressure swing adsorption process defines a higher pressure and a lower pressure, and wherein the higher pressure is between about 130-230 psig.

9. An adsorptive gas separation process for producing a purified methane product gas from a feed gas mixture comprising methane and carbon dioxide, the process comprising the sequential steps of:

contacting the feed gas mixture with a first adsorbent material suited for adsorbing a majority of the carbon dioxide in the feed gas stream, wherein the first adsorbent material is selected from the group consisting of aluminas, silicas, silica gel, hydrophohic zeolites, activated carbon and combinations thereof; and contacting the gas mixture with a second adsorbent material suited for substantially removing remaining amounts of carbon dioxide while substantially excluding methane from adsorption, wherein the second adsorbent material is selected from the group consisting of zeolite 3A, carbon molecular sieves, titanosilicate molecular sieve materials and combinations thereof; and wherein the process further includes vacuum assisted desorption of the first adsorbent material and the second adsorbent material during regeneration.

10. The process of claim 9 wherein the process is a pressure swing adsorption process.

11. The process of claim 9 wherein the first adsorbent material comprises activated alumina.

12. The process of claim 11 wherein the first adsorbent material additionally comprises silica gel.

13. The process of claim 9 wherein the first adsorbent material is activated alumina and the second adsorbent material is a carbon molecular sieve.

14. The process of claim 9 wherein the feed gas mixture comprises at least about 10% carbon dioxide.

15. The process of claim 9 wherein the purified methane product gas comprises less than about 5000 ppm carbon dioxide.

16. The adsorptive gas separation process according to claim 9 wherein the feed gas mixture comprises at least about 20% carbon dioxide.

17. The adsorptive gas separation process according to claim 9 wherein the feed gas mixture comprises at least about 50% carbon dioxide.

18. The adsorptive gas separation process according to claim 9 wherein the purified methane product gas contains less than about 1000 ppm of carbon dioxide.

19. The adsorptive gas separation process according to claim 9 wherein the purified methane product gas contains less than about 100 ppm of carbon dioxide.

20. The adsorptive gas separation process according to claim 10 wherein the pressure swing adsorption process defines a higher pressure and a lower pressure, and wherein the higher pressure is between about 100-250 psig.

21. The adsorptive gas separation process according to claim 10 wherein the pressure swing adsorption process defines a higher pressure and a lower pressure, and wherein the higher pressure is between about 130-230 psig.

* * * * *